United States Patent [19]

Gondar et al.

[11] Patent Number: 4,886,009

[45] Date of Patent: Dec. 12, 1989

[54] COMPOSITE TOOL HAVING WEAR INDICATOR

[75] Inventors: Robert K. Gondar, Monroe; Philip J. Jacobs, Northford, both of Conn.

[73] Assignee: United Technologies Corporation, Hartford, Conn.

[21] Appl. No.: 211,949

[22] Filed: Jun. 27, 1988

[51] Int. Cl.⁴ .................... G01N 3/56; B24B 55/00
[52] U.S. Cl. .................... 116/208; 51/165.87; 51/281 R; 408/116
[58] Field of Search .......... 116/208; 138/36; 408/145, 116, 16; 51/281 R, 326; 73/7

[56] References Cited

U.S. PATENT DOCUMENTS

| | | | |
|---|---|---|---|
| 3,050,027 | 8/1962 | Borneman | 116/208 X |
| 3,414,272 | 12/1968 | Rogers, Jr. | 116/208 X |
| 3,842,792 | 10/1974 | Souther | 116/208 |
| 4,095,552 | 6/1978 | Lo | 116/208 |
| 4,640,057 | 2/1987 | Salje | 51/165.87 |
| 4,680,897 | 7/1987 | Daniels et al. | 51/281 R |
| 4,720,218 | 1/1988 | De Fries et al. | 408/145 |

FOREIGN PATENT DOCUMENTS 0261749  6/1968  U.S.S.R. .................. 116/208

Primary Examiner—Daniel M. Yasich

[57] ABSTRACT

An indicator that provides information on the wear status of a composite tool that is subject to abrasion during use. The composite tool contains at least one wear groove in the area subject to abrasion. The wear groove has a desired length and predetermined depth. The wear groove is formed of a desired length and of a predetermined depth into the tool in the area subject to abrasion. During use of the tool in composite forming, the tool is inspected for the presence and depth of the wear groove thereby indicating the wear status of the tool.

8 Claims, 1 Drawing Sheet 4,886,009

COMPOSITE TOOL HAVING WEAR INDICATOR

DESCRIPTION

1. Technical Field

This invention relates to composite tools and an inspection method for monitoring said tools and particularly methods for ensuring that the tools' dimensional tolerances are maintained.

2. Background Art

Composite components have become commonplace in the aerospace industry. Because of their widespread use there is continuing investigation and research into methods and apparatuses for making and trimming composite parts. Composite components, particularly those which are not primary load bearing structures, are typically formed oversize and trimmed to net dimensions via a gerber, laser or water-jet type cutter. Commonly, a guide or pattern tool is provided for aiding the operator in establishing the proper dimensional tolerance of the part produced. Metal tools have in the past been utilized for such trimming procedures inasmuch as they exhibit excellent wear resistance to the abrasion of the cutting edge or means. Such guide tools, however, can be costly to produce, especially when high rate production demands multiple tools, and are precluded from use when the component is of a size such that the corresponding tool would be unmanageably weighty. Accordingly, composite materials such as epoxy resin and fiberglass are becoming increasingly popular since they can be readily molded and trimmed to shape (rather than NC (numerically controlled) machined) and are lighter in weight, hence offering greater utility. Unfortunately, composite tools are more susceptible to wear than conventional metal tools. As a result, the tools must be periodically inspected to ascertain whether they remain within predetermined dimensional tolerance limits. These inspections can require numerous measurements by a skilled inspector. Consequently, the inspections result in increased cost and tool control problems.

Accordingly, there has been a continual search in this field of art for methods of simplifying the inspection of composite tools for wear.

DISCLOSURE OF THE INVENTION

This invention is directed to an indicator that provides information on the wear status of a composite tool that is subject to abrasion during use. The composite tool contains at least one wear groove in the area subject to abrasion. The wear groove has a desired length and predetermined depth.

Another aspect of this invention relates to an inspection method for determining whether the dimensional tolerances of a composite tool, subject to abrasion during use, are within predetermined limits. The method comprises forming a wear groove of a desired length and of a predetermined depth into the tool in the area subject to abrasion. During use of the tool in composite forming, the tool is inspected for the presence and depth of the wear groove thereby indicating the wear status of the tool.

The foregoing and other objects, features and advantages will be apparent from the specification, claims and from the accompanying drawings which will illustrate an embodiment of the invention.

BEST MODE FOR CARRYING OUT THE INVENTION

Figure 1:
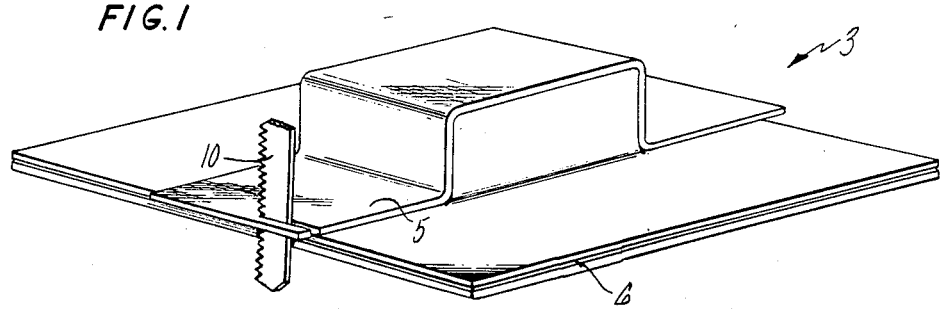
FIG. 1 is a perspective view of a composite tool of this invention including wear grooves.
Figure 1A:
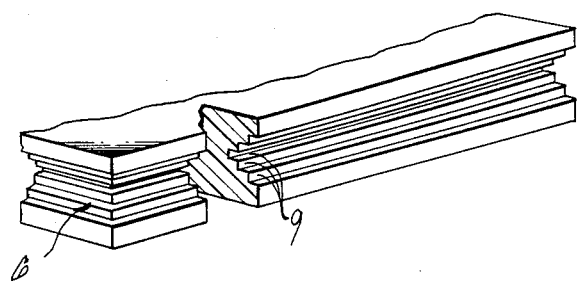
FIG. 1A is an enlarged view partly broken away and partly in section of the wear grooves of this invention.
Figure 1B:
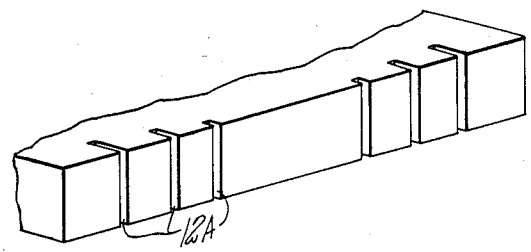
FIGS. 1B and 1C illustrate alternate embodiments of the wear indicator.
Figure 1C:
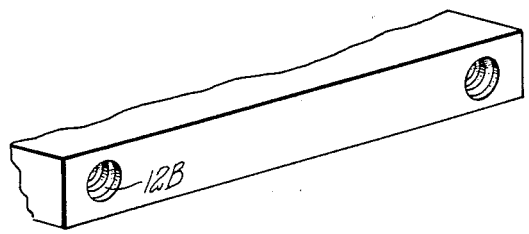

According to the Figure, composite 5 is disposed on the rectangular portion of composite guide tool 3. Cutting means 10 trims the composite 5 to the dimension of the composite guide tool 3 extending therefrom. The composite tool 3 has a wear groove 6 of a predetermined depth. The wear groove 6 can have a plurality of steps 9 of various depths. Alternatively, as shown in FIGS. 1A and 1B respectively, a plurality of wear grooves and step holes 12A and 12B of various depths may be used.

The wear groove(s) are typically located on the tool 3 in the areas that are subject to the abrasion and wear of cutting/trimming devices used in conjunction therewith. Typically, these areas are also the same surfaces subjected to wear and abrasion during tool storage. Generally in composite manufacturing, this occurs along the edge of the tool, however, it may occur elsewhere such as blank stops and locating surfaces where the manufactured part or tool meet.

Any wear groove or combination of wear grooves may be used that provides the desired information. Thus, one wear groove having a sufficient depth may be all that is needed to provide notice of a tool whose dimensions are no longer within specification due to wear. Alternatively, a wear groove having several steps of various depths provides more detailed information on the wear status of the tool during its use over many manufacturing cycles. Other possibilities can also be envisioned by those skilled in the art.

The dimensions of the wear groove should (like the type of wear groove) be such as to provide the desired information on tool wear. The most important dimension is the groove depth. The predetermined depth should supply the above information. An exemplary depth may be slightly less than the dimensional tolerance of the tool. However, about ½ this dimension is considered a preferable depth. Hence, if the dimensional tolerance of the tool is 0.020 inches, a wear groove depth of 0.010 is recommended. Since tolerances of highly to marginally accurate tools typically range from about 0.010 to about 0.060 inches, wear groove depths will typically range from about 0.005 to about 0.030 inches. Thus, when the groove is first no longer visible or barely visible it is time to remove the tool from service for refurbishing. A wear groove that has steps provides advantages since a safety margin of one step can be used as an indicator. The depths of steps typically range from about 0.005 to about 0.010.

The length of the wear groove is determined by the area of wear on the tool. A larger wear area necessitates a longer wear groove (or a series of short grooves). The width of the wear groove is as desired, however, it is typically a function of the depth, for example, conventional cutters have a 90° included angle. Typically, the width is about 0.030 to about 0.120 inches.

The wear grooves may be made by a variety of methods known to those skilled in the art such as routers or bar mounted saws, rotary files, etc. Methods that provide for easy control of the dimensions of the grooves work best.

The wear groove(s) may also be color coded. For example, a single groove could be painted or impregnated with a color contrasting to that of the tool edge such that visual inspection thereof will be enhanced or similarly multiple or stepped grooves painted a variety of colors could be employed for yielding the same effect.

During composite manufacturing the tools provided with the wear grooves are inspected for the presence and/or depth of the wear grooves. Typically, the inspection is a simple visual inspection however other methods may be envisioned such as measurement with a flush pin indicator gage. This method provides a simple reference point since the wear grooves are made prior to any wear. In contrast dimensional measurements of a tool that doesn't have wear grooves is time consuming since there is no reference point.

Thus, this invention obviates the need for highly skilled tool inspectors to use metrology instruments and provides a method of inspecting tools for wear that can be done visually by lesser skilled personnel. In addition, it reduces the need for cycling tools through periodic tool inspections.

It should be understood that the invention is not limited to the particular embodiments shown and described herein, but that various changes and modifications may be made without departing from the spirit and scope of this novel concept as defined by the following claims.

We claim:

1. A tool particularly adapted for forming of a composite material shape comprising a composite guide tool having a guide edge that is subject to abrasion from a cutting means, said tool containing at least one wear groove in at least one of said guide edges that is subjected to said abrasion, said wear groove of a desired length and of a predetermined depth.

2. The composite forming guide tool as recited in claim 1 wherein said wear groove has steps of various predetermined depths.

3. The composite formin guide tool as recited in claim 1 having a plurality of wear grooves of various predetermined depths.

4. The composite forming guide tool as recited in claim 1 wherein said wear groove depth is slightly less than the predetermined dimensional tolerance limit of the tool.

5. An inspection method for determining whether the dimensional tolerances of a composite tool having a guide edge that is subject to abrasion from a cutting means, are within predetermined limits comprising:
   a. forming a wear groove of a desired length and of a predetermined depth in at least one of said guide edges that is subjected to said abrasion; and
   b. inspecting the tool during use, in forming of a composite material shape, for the presence and depth of the wear groove thereby indicating the wear status of the tool.

6. The method as recited in claim 5 wherein said wear groove contains steps of various predetermined depths.

7. The method as reoited in claim 5 wherein a plurality of wear grooves of various predetermined depths are cut.

8. The method as recited in claim 5 wherein said wear grooves have a depth slightly less than the predetermined dimensional tolerance limit of the tool.

* * * * *